(12) United States Patent
Black et al.

(10) Patent No.: US 7,199,224 B2
(45) Date of Patent: *Apr. 3, 2007

(54) ANTIBODIES THAT BIND TNF-α CONVERTING ENZYME

(75) Inventors: Roy A Black, Seattle, WA (US); Charles Rauch, Bainbridge Island, WA (US); Carl J March, Bainbridge Island, WA (US); Douglas P Cerretti, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 601 days.

This patent is subject to a terminal disclaimer.

(21) Appl. No.: 10/423,729

(22) Filed: Apr. 25, 2003

(65) Prior Publication Data
US 2003/0175816 A1    Sep. 18, 2003

Related U.S. Application Data

(60) Division of application No. 09/726,968, filed on Nov. 29, 2000, now Pat. No. 6,555,354, which is a division of application No. 09/579,766, filed on May 26, 2000, now Pat. No. 6,406,901, which is a division of application No. 09/440,324, filed on Nov. 15, 1999, now abandoned, which is a continuation of application No. 09/183,275, filed on Oct. 30, 1998, now Pat. No. 6,013,466, which is a continuation of application No. 08/655,345, filed on May 23, 1996, now Pat. No. 5,830,742.

(60) Provisional application No. 60/033,750, filed on Jul. 20, 1995, provisional application No. 60/033,169, filed on Jun. 8, 1995.

(51) Int. Cl.
C07K 16/00    (2006.01)

(52) U.S. Cl. .................. 530/387.1; 530/300; 530/350; 530/388.1; 530/351; 435/226; 435/219

(58) Field of Classification Search .............. 530/350, 530/387.1, 388.1, 300, 351; 435/226, 219
See application file for complete search history.

(56) References Cited

U.S. PATENT DOCUMENTS

| 5,422,425 A | 6/1995 | Krieger |
|---|---|---|
| 5,545,518 A | 8/1996 | Krieger |
| 5,594,106 A | 1/1997 | Black |
| 5,629,285 A | 5/1997 | Black |
| 5,691,382 A | 11/1997 | Crimmin |
| 5,702,705 A | 12/1997 | Kriegler |
| 5,753,653 A | 5/1998 | Bender |
| 5,830,742 A | 11/1998 | Black |
| 5,998,378 A | 12/1999 | Krieger |
| 6,013,466 A | 1/2000 | Black |
| 6,180,403 B1 | 1/2001 | Fluornoy |

FOREIGN PATENT DOCUMENTS

| EP | 0 592 423 B1 | 11/2000 |
|---|---|---|
| WO | WO91/02756 A1 | 3/1991 |
| WO | WO92/00378 A1 | 1/1992 |
| WO | WO92/02822 A1 | 2/1992 |
| WO | WO94/00555 A2 | 1/1994 |
| WO | WO94/10990 A1 | 5/1994 |
| WO | WO94/24140 A1 | 10/1994 |
| WO | WO95/06031 A1 | 3/1995 |
| WO | WO95/09841 A1 | 4/1995 |
| WO | WO95/24501 A1 | 9/1995 |
| WO | WO96/33176 A1 | 10/1996 |
| WO | WO96/35712 A1 | 11/1996 |
| WO | WO96/35714 A1 | 11/1996 |
| WO | WO97/35538 A2 | 10/1997 |
| WO | WO99/40182 A2 | 8/1999 |
| WO | WO99/40182 A3 | 8/1999 |
| WO | WO00/09492 A1 | 2/2000 |
| WO | WO91/02540 A1 | 3/2001 |

OTHER PUBLICATIONS

U.S. Appl. No. 09/244,984, filed Feb 4, 1999, Black.
Krieger et al., "A Novel Form of TNF/Cachectin is a Cell Surface Cytotoxic Transmembrane Protein: Ramifications for the Complex Physiology of TNF," *Cell* 535-53, 1988.
Scuderi, P., "Suppression of Human Leukocyte Tumor Necrosis Factor Secretion by the Serine Protease Inhibitor p-Toluenesulfonyl-L-Arginine Methyl Ester (TAME)," *J. Immunology* 143 168-173, 1989.
Davis B et al., "A Synthetic Matrix Metalloproteinase Inhibitor Decreases Tumor Burden and Prolongs Survival of Mice Bearing Human Ovarian Carcinoma Xenografts," *Cancer Res.* 53:2087-2091, 1993.
Hell, W., et al., "Cleavage of tumor necrosis factor-α by Legionella exoprotease," *APMIS* 101:120-126, 1993.
Mohler, K. et al., "Protection against a lethal dose of endotoxin by an inhibitor of tumour necrosis factor processing," *Nature* 370:218-220, 1994.
Gearing, A. et al., "Processing of Tumour necrosis factor-α precursor by metalloproteinases," *Nature* 370:555-557, 1994.
McGeehan, G. et al., "Regulation of tumour necrosis factorα processing by a metalloproteinase inhibitor," *Nature* 370:558-561, 1994.
Black et al., "Cloning of a Membrane-Bound TNFα Converting Enzyme (TACE)," *Eur Cytokine Netw* 7:180, Apr.-Jun. 1996.

(Continued)

Primary Examiner—Jennifer E. Graser
(74) Attorney, Agent, or Firm—Suzanne A. Sprunger; Susan E. Lingenfelter

(57) ABSTRACT

A metalloprotease that converts TNF-α from the 26 kD cell form to the 17 kD form has been isolated and purified and the cDNA sequence known. In particular, the protease has a molecular weight of approximately 80 kD. The isolated and purified protease is useful for designing an inhibitor thereof, and may find use as a therapeutic agent. Assays for detecting the protease-inhibiting activity of a molecule are also an aspect of the invention.

13 Claims, No Drawings

OTHER PUBLICATIONS

Moss M., et al., "Structural Features and Biochemical Properties of TNF-Alpha Convertase," *Eur. Cytokine Netw.* 7:181, Apr.-Jun. 1996.

Gearing A. "ATNF and Matrix Mettaloproteinase Inhibitors,", *Eur. Cytokine Netw.* 7:284, Apr.-Jun. 1996.

Liedtke W., et al., "A Matrix Mettaloprotease Inhibitor is Effective in Acute and Chronic Recurrent Experimental Allergic Encephalomyelitis (EAE),"*Eur. Cytokine Netw.* 7:284, Apr.-Jun. 1996.

Wallach D., "A Decade of Accumulated Knowledge and Emerging Answers," *Eur. Cytokine Netw.* 7:713-724, Dec. 1996.

Black, R. et al. "A Metalloproteinase Disintegrin that Releases Tumour-Necrosis Factor-α from Cells," *Nature* 385:729-732, 1997.

Moss, M. et al., "Cloning of a Disintegrin Metalloproteinase that Processes Precursor Tumour Necrosis Factor α," *Nature* 385: 733-736, 1997.

Armour, A. et al., "TNF-alpha Converting Enzyme (TACE) is Inhibited by TIMP-3," *FEBS lett.* 435:39-44, 1998.

SEQUENCE LISTING

```
<160> NUMBER OF SEQ ID NOS: 9

<210> SEQ ID NO 1
<211> LENGTH: 2475
<212> TYPE: DNA
<213> ORGANISM: Homo sapiens
```

```
<220> FEATURE:
<221> NAME/KEY: CDS
<222> LOCATION: (1)..(2472)

<400> SEQUENCE: 1 atg agg cag tct ctc cta ttc ctg acc agc gtg gtt cct ttc gtg ctg     48
Met Arg Gln Ser Leu Leu Phe Leu Thr Ser Val Val Pro Phe Val Leu
 1               5                  10                  15 gcg ccg cga cct ccg gat gac ccg ggc ttc ggc ccc cac cag aga ctc     96
Ala Pro Arg Pro Pro Asp Asp Pro Gly Phe Gly Pro His Gln Arg Leu
            20                  25                  30 gag aag ctt gat tct ttg ctc tca gac tac gat att ctc tct tta tct    144
Glu Lys Leu Asp Ser Leu Leu Ser Asp Tyr Asp Ile Leu Ser Leu Ser
        35                  40                  45 aat atc cag cag cat tcg gta aga aaa aga gat cta cag act tca aca    192
Asn Ile Gln Gln His Ser Val Arg Lys Arg Asp Leu Gln Thr Ser Thr
 50                  55                  60 cat gta gaa aca cta cta act ttt tca gct ttg aaa agg cat ttt aaa    240
His Val Glu Thr Leu Leu Thr Phe Ser Ala Leu Lys Arg His Phe Lys
 65                  70                  75                  80 tta tac ctg aca tca agt act gaa cgt ttt tca caa aat ttc aag gtc    288
Leu Tyr Leu Thr Ser Ser Thr Glu Arg Phe Ser Gln Asn Phe Lys Val
                85                  90                  95 gtg gtg gtg gat ggt aaa aac gaa agc gag tac act gta aaa tgg cag    336
Val Val Val Asp Gly Lys Asn Glu Ser Glu Tyr Thr Val Lys Trp Gln
            100                 105                 110 gac ttc ttc act gga cac gtg gtt ggt gag cct gac tct agg gtt cta    384
Asp Phe Phe Thr Gly His Val Val Gly Glu Pro Asp Ser Arg Val Leu
        115                 120                 125 gcc cac ata aga gat gat gat gtt ata atc aga atc aac aca gat ggg    432
Ala His Ile Arg Asp Asp Asp Val Ile Ile Arg Ile Asn Thr Asp Gly
130                 135                 140 gcc gaa tat aac ata gag cca ctt tgg aga ttt gtt aat gat acc aaa    480
Ala Glu Tyr Asn Ile Glu Pro Leu Trp Arg Phe Val Asn Asp Thr Lys
145                 150                 155                 160 gac aaa aga atg tta gtt tat aaa tct gaa gat atc aag aat gtt tca    528
Asp Lys Arg Met Leu Val Tyr Lys Ser Glu Asp Ile Lys Asn Val Ser
                165                 170                 175 cgt ttg cag tct cca aaa gtg tgt ggt tat tta aaa gtg gat aat gaa    576
Arg Leu Gln Ser Pro Lys Val Cys Gly Tyr Leu Lys Val Asp Asn Glu
            180                 185                 190 gag ttg ctc cca aaa ggg tta gta gac aga gaa cca cct gaa gag ctt    624
Glu Leu Leu Pro Lys Gly Leu Val Asp Arg Glu Pro Pro Glu Glu Leu
        195                 200                 205 gtt cat cga gtg aaa aga aga gct gac cca gat ccc atg aag aac acg    672
Val His Arg Val Lys Arg Arg Ala Asp Pro Asp Pro Met Lys Asn Thr
    210                 215                 220 tgt aaa tta ttg gtg gta gca gat cat cgc ttc tac aga tac atg ggc    720
Cys Lys Leu Leu Val Val Ala Asp His Arg Phe Tyr Arg Tyr Met Gly
225                 230                 235                 240 aga ggg gaa gag agt aca act aca aat tac tta ata gag cta att gac    768
Arg Gly Glu Glu Ser Thr Thr Thr Asn Tyr Leu Ile Glu Leu Ile Asp
                245                 250                 255 aga gtt gat gac atc tat cgg aac act tca tgg gat aat gca ggt ttt    816
Arg Val Asp Asp Ile Tyr Arg Asn Thr Ser Trp Asp Asn Ala Gly Phe
            260                 265                 270 aaa ggc tat gga ata cag ata gag cag att cgc att ctc aag tct cca    864
Lys Gly Tyr Gly Ile Gln Ile Glu Gln Ile Arg Ile Leu Lys Ser Pro
        275                 280                 285 caa gag gta aaa cct ggt gaa aag cac tac aac atg gca aaa agt tac    912
```

```
                Gln Glu Val Lys Pro Gly Glu Lys His Tyr Asn Met Ala Lys Ser Tyr
                    290                 295                 300 cca aat gaa gaa aag gat gct tgg gat gtg aag atg ttg cta gag caa         960
Pro Asn Glu Glu Lys Asp Ala Trp Asp Val Lys Met Leu Leu Glu Gln
305                 310                 315                 320 ttt agc ttt gat ata gct gag gaa gca tct aaa gtt tgc ttg gca cac        1008
Phe Ser Phe Asp Ile Ala Glu Glu Ala Ser Lys Val Cys Leu Ala His
                325                 330                 335 ctt ttc aca tac caa gat ttt gat atg gga act ctt gga tta gct tat        1056
Leu Phe Thr Tyr Gln Asp Phe Asp Met Gly Thr Leu Gly Leu Ala Tyr
                340                 345                 350 gtt ggc tct ccc aga gca aac agc cat gga ggt gtt tgt cca aag gct        1104
Val Gly Ser Pro Arg Ala Asn Ser His Gly Gly Val Cys Pro Lys Ala
            355                 360                 365 tat tat agc cca gtt ggg aag aaa aat atc tat ttg aat agt ggt ttg        1152
Tyr Tyr Ser Pro Val Gly Lys Lys Asn Ile Tyr Leu Asn Ser Gly Leu
    370                 375                 380 acg agc aca aag aat tat ggt aaa acc atc ctt aca aag gaa gct gac        1200
Thr Ser Thr Lys Asn Tyr Gly Lys Thr Ile Leu Thr Lys Glu Ala Asp
385                 390                 395                 400 ctg gtt aca act cat gaa ttg gga cat aat ttt gga gca gaa cat gat        1248
Leu Val Thr Thr His Glu Leu Gly His Asn Phe Gly Ala Glu His Asp
                405                 410                 415 ccg gat ggt cta gca gaa tgt gcc ccg aat gag gac cag gga ggg aaa        1296
Pro Asp Gly Leu Ala Glu Cys Ala Pro Asn Glu Asp Gln Gly Gly Lys
                420                 425                 430 tat gtc atg tat ccc ata gct gtg agt ggc gat cac gag aac aat aag        1344
Tyr Val Met Tyr Pro Ile Ala Val Ser Gly Asp His Glu Asn Asn Lys
            435                 440                 445 atg ttt tca aac tgc agt aaa caa tca atc tat aag acc att gaa agt        1392
Met Phe Ser Asn Cys Ser Lys Gln Ser Ile Tyr Lys Thr Ile Glu Ser
    450                 455                 460 aag gcc cag gag tgt ttt caa gaa cgc agc aat aaa gtt tgt ggg aac        1440
Lys Ala Gln Glu Cys Phe Gln Glu Arg Ser Asn Lys Val Cys Gly Asn
465                 470                 475                 480 tcg agg gtg gat gaa gga gaa gag tgt gat cct ggc atc atg tat ctg        1488
Ser Arg Val Asp Glu Gly Glu Glu Cys Asp Pro Gly Ile Met Tyr Leu
                485                 490                 495 aac aac gac acc tgc tgc aac agc gac tgc acg ttg aag gaa ggt gtc        1536
Asn Asn Asp Thr Cys Cys Asn Ser Asp Cys Thr Leu Lys Glu Gly Val
                500                 505                 510 cag tgc agt gac agg aac agt cct tgc tgt aaa aac tgt cag ttt gag        1584
Gln Cys Ser Asp Arg Asn Ser Pro Cys Cys Lys Asn Cys Gln Phe Glu
            515                 520                 525 act gcc cag aag aag tgc cag gag gcg att aat gct act tgc aaa ggc        1632
Thr Ala Gln Lys Lys Cys Gln Glu Ala Ile Asn Ala Thr Cys Lys Gly
    530                 535                 540 gtg tcc tac tgc aca ggt aat agc agt gag tgc ccg cct cca gga aat        1680
Val Ser Tyr Cys Thr Gly Asn Ser Ser Glu Cys Pro Pro Pro Gly Asn
545                 550                 555                 560 gct gaa gat gac act gtt tgc ttg gat ctt ggc aag tgt aag gat ggg        1728
Ala Glu Asp Asp Thr Val Cys Leu Asp Leu Gly Lys Cys Lys Asp Gly
                565                 570                 575 aaa tgc atc cct ttc tgc gag agg gaa cag cag ctg gag tcc tgt gca        1776
Lys Cys Ile Pro Phe Cys Glu Arg Glu Gln Gln Leu Glu Ser Cys Ala
                580                 585                 590 tgt aat gaa act gac aac tcc tgc aag gtg tgc tgc agg gac ctt tcc        1824
Cys Asn Glu Thr Asp Asn Ser Cys Lys Val Cys Cys Arg Asp Leu Ser
            595                 600                 605
```

```
ggc cgc tgt gtg ccc tat gtc gat gct gaa caa aag aac tta ttt ttg      1872
Gly Arg Cys Val Pro Tyr Val Asp Ala Glu Gln Lys Asn Leu Phe Leu
    610             615                 620 agg aaa gga aag ccc tgt aca gta gga ttt tgt gac atg aat ggc aaa      1920
Arg Lys Gly Lys Pro Cys Thr Val Gly Phe Cys Asp Met Asn Gly Lys
625                 630                 635                 640 tgt gag aaa cga gta cag gat gta att gaa cga ttt tgg gat ttc att      1968
Cys Glu Lys Arg Val Gln Asp Val Ile Glu Arg Phe Trp Asp Phe Ile
                    645                 650                 655 gac cag ctg agc atc aat act ttt gga aag ttt tta gca gac aac atc      2016
Asp Gln Leu Ser Ile Asn Thr Phe Gly Lys Phe Leu Ala Asp Asn Ile
                660                 665                 670 gtt ggg tct gtc ctg gtt ttc tcc ttg ata ttt tgg att cct ttc agc      2064
Val Gly Ser Val Leu Val Phe Ser Leu Ile Phe Trp Ile Pro Phe Ser
            675                 680                 685 att ctt gtc cat tgt gtg gat aag aaa ttg gat aaa cag tat gaa tct      2112
Ile Leu Val His Cys Val Asp Lys Lys Leu Asp Lys Gln Tyr Glu Ser
        690                 695                 700 ctg tct ctg ttt cac ccc agt aac gtc gaa atg ctg agc agc atg gat      2160
Leu Ser Leu Phe His Pro Ser Asn Val Glu Met Leu Ser Ser Met Asp
705                 710                 715                 720 tct gca tcg gtt cgc att atc aaa ccc ttt cct gcg ccc cag act cca      2208
Ser Ala Ser Val Arg Ile Ile Lys Pro Phe Pro Ala Pro Gln Thr Pro
                    725                 730                 735 ggc cgc ctg cag cct gcc cct gtg atc cct tcg gcg cca gca gct cca      2256
Gly Arg Leu Gln Pro Ala Pro Val Ile Pro Ser Ala Pro Ala Ala Pro
                740                 745                 750 aaa ctg gac cac cag aga atg gac acc atc cag gaa gac ccc agc aca      2304
Lys Leu Asp His Gln Arg Met Asp Thr Ile Gln Glu Asp Pro Ser Thr
            755                 760                 765 gac tca cat atg gac gag gat ggg ttt gag aag gac ccc ttc cca aat      2352
Asp Ser His Met Asp Glu Asp Gly Phe Glu Lys Asp Pro Phe Pro Asn
        770                 775                 780 agc agc aca gct gcc aag tca ttt gag gat ctc acg gac cat ccg gtc      2400
Ser Ser Thr Ala Ala Lys Ser Phe Glu Asp Leu Thr Asp His Pro Val
785                 790                 795                 800 acc aga agt gaa aag gct gcc tcc ttt aaa ctg cag cgt cag aat cgt      2448
Thr Arg Ser Glu Lys Ala Ala Ser Phe Lys Leu Gln Arg Gln Asn Arg
                    805                 810                 815 gtt gac agc aaa gaa aca gag tgc taa                                  2475
Val Asp Ser Lys Glu Thr Glu Cys
                820

<210> SEQ ID NO 2
<211> LENGTH: 824
<212> TYPE: PRT
<213> ORGANISM: Homo sapiens

<400> SEQUENCE: 2

Met Arg Gln Ser Leu Leu Phe Leu Thr Ser Val Val Pro Phe Val Leu
 1               5                  10                  15

Ala Pro Arg Pro Pro Asp Asp Pro Gly Phe Gly Pro His Gln Arg Leu
            20                  25                  30

Glu Lys Leu Asp Ser Leu Leu Ser Asp Tyr Asp Ile Leu Ser Leu Ser
        35                  40                  45

Asn Ile Gln Gln His Ser Val Arg Lys Arg Asp Leu Gln Thr Ser Thr
    50                  55                  60

His Val Glu Thr Leu Leu Thr Phe Ser Ala Leu Lys Arg His Phe Lys
65                  70                  75                  80
```

```
Leu Tyr Leu Thr Ser Ser Thr Glu Arg Phe Ser Gln Asn Phe Lys Val
                85                  90                  95
Val Val Val Asp Gly Lys Asn Glu Ser Glu Tyr Thr Val Lys Trp Gln
            100                 105                 110
Asp Phe Phe Thr Gly His Val Val Gly Glu Pro Asp Ser Arg Val Leu
                115                 120                 125
Ala His Ile Arg Asp Asp Val Ile Ile Arg Ile Asn Thr Asp Gly
130                 135                 140
Ala Glu Tyr Asn Ile Glu Pro Leu Trp Arg Phe Val Asn Asp Thr Lys
145                 150                 155                 160
Asp Lys Arg Met Leu Val Tyr Lys Ser Glu Ile Lys Asn Val Ser
                165                 170                 175
Arg Leu Gln Ser Pro Lys Val Cys Gly Tyr Leu Lys Val Asp Asn Glu
                180                 185                 190
Glu Leu Leu Pro Lys Gly Leu Val Asp Arg Glu Pro Glu Glu Leu
            195                 200                 205
Val His Arg Val Lys Arg Arg Ala Asp Pro Asp Pro Met Lys Asn Thr
    210                 215                 220
Cys Lys Leu Leu Val Val Ala Asp His Arg Phe Tyr Arg Tyr Met Gly
225                 230                 235                 240
Arg Gly Glu Glu Ser Thr Thr Thr Asn Tyr Leu Ile Glu Leu Ile Asp
                245                 250                 255
Arg Val Asp Asp Ile Tyr Arg Asn Thr Ser Trp Asp Asn Ala Gly Phe
                260                 265                 270
Lys Gly Tyr Gly Ile Gln Ile Glu Gln Ile Arg Ile Leu Lys Ser Pro
            275                 280                 285
Gln Glu Val Lys Pro Gly Glu Lys His Tyr Asn Met Ala Lys Ser Tyr
    290                 295                 300
Pro Asn Glu Glu Lys Asp Ala Trp Asp Val Lys Met Leu Leu Glu Gln
305                 310                 315                 320
Phe Ser Phe Asp Ile Ala Glu Ala Ser Lys Val Cys Leu Ala His
                325                 330                 335
Leu Phe Thr Tyr Gln Asp Phe Asp Met Gly Thr Leu Gly Leu Ala Tyr
            340                 345                 350
Val Gly Ser Pro Arg Ala Asn Ser His Gly Gly Val Cys Pro Lys Ala
        355                 360                 365
Tyr Tyr Ser Pro Val Gly Lys Lys Asn Ile Tyr Leu Asn Ser Gly Leu
    370                 375                 380
Thr Ser Thr Lys Asn Tyr Gly Lys Thr Ile Leu Thr Lys Glu Ala Asp
385                 390                 395                 400
Leu Val Thr Thr His Glu Leu Gly His Asn Phe Gly Ala Glu His Asp
                405                 410                 415
Pro Asp Gly Leu Ala Glu Cys Ala Pro Asn Glu Asp Gln Gly Gly Lys
            420                 425                 430
Tyr Val Met Tyr Pro Ile Ala Val Ser Gly Asp His Glu Asn Asn Lys
        435                 440                 445
Met Phe Ser Asn Cys Ser Lys Gln Ser Ile Tyr Lys Thr Ile Glu Ser
    450                 455                 460
Lys Ala Gln Glu Cys Phe Gln Glu Arg Ser Asn Lys Val Cys Gly Asn
465                 470                 475                 480
Ser Arg Val Asp Glu Gly Glu Glu Cys Asp Pro Gly Ile Met Tyr Leu
            485                 490                 495
Asn Asn Asp Thr Cys Cys Asn Ser Asp Cys Thr Leu Lys Glu Gly Val
```

-continued

```
                        500                 505                 510
        Gln Cys Ser Asp Arg Asn Ser Pro Cys Cys Lys Asn Cys Gln Phe Glu
                    515                 520                 525

Thr Ala Gln Lys Lys Cys Gln Glu Ala Ile Asn Ala Thr Cys Lys Gly
                    530                 535                 540

Val Ser Tyr Cys Thr Gly Asn Ser Ser Glu Cys Pro Pro Gly Asn
        545                 550                 555                 560

Ala Glu Asp Asp Thr Val Cys Leu Asp Leu Gly Lys Cys Lys Asp Gly
                            565                 570                 575

Lys Cys Ile Pro Phe Cys Glu Arg Glu Gln Gln Leu Glu Ser Cys Ala
                        580                 585                 590

Cys Asn Glu Thr Asp Asn Ser Cys Lys Val Cys Cys Arg Asp Leu Ser
                    595                 600                 605

Gly Arg Cys Val Pro Tyr Val Asp Ala Glu Gln Lys Asn Leu Phe Leu
                610                 615                 620

Arg Lys Gly Lys Pro Cys Thr Val Gly Phe Cys Asp Met Asn Gly Lys
        625                 630                 635                 640

Cys Glu Lys Arg Val Gln Asp Val Ile Glu Arg Phe Trp Asp Phe Ile
                            645                 650                 655

Asp Gln Leu Ser Ile Asn Thr Phe Gly Lys Phe Leu Ala Asp Asn Ile
                        660                 665                 670

Val Gly Ser Val Leu Val Phe Ser Leu Ile Phe Trp Ile Pro Phe Ser
                    675                 680                 685

Ile Leu Val His Cys Val Asp Lys Lys Leu Asp Lys Gln Tyr Glu Ser
                690                 695                 700

Leu Ser Leu Phe His Pro Ser Asn Val Glu Met Leu Ser Ser Met Asp
        705                 710                 715                 720

Ser Ala Ser Val Arg Ile Ile Lys Pro Phe Pro Ala Pro Gln Thr Pro
                            725                 730                 735

Gly Arg Leu Gln Pro Ala Pro Val Ile Pro Ser Ala Pro Ala Ala Pro
                        740                 745                 750

Lys Leu Asp His Gln Arg Met Asp Thr Ile Gln Glu Asp Pro Ser Thr
                    755                 760                 765

Asp Ser His Met Asp Glu Asp Gly Phe Glu Lys Asp Pro Phe Pro Asn
                770                 775                 780

Ser Ser Thr Ala Ala Lys Ser Phe Glu Asp Leu Thr Asp His Pro Val
        785                 790                 795                 800

Thr Arg Ser Glu Lys Ala Ala Ser Phe Lys Leu Gln Arg Gln Asn Arg
                            805                 810                 815

Val Asp Ser Lys Glu Thr Glu Cys
                        820

<210> SEQ ID NO 3
<211> LENGTH: 2097
<212> TYPE: DNA
<213> ORGANISM: Homo sapiens
<220> FEATURE:
<221> NAME/KEY: CDS
<222> LOCATION: (1)..(2094)

<400> SEQUENCE: 3 atg agg cag tct ctc cta ttc ctg acc agc gtg gtt cct ttc gtg ctg       48
Met Arg Gln Ser Leu Leu Phe Leu Thr Ser Val Val Pro Phe Val Leu
  1               5                  10                  15 gcg ccg cga cct ccg gat gac ccg ggc ttc ggc ccc cac cag aga ctc       96
Ala Pro Arg Pro Pro Asp Asp Pro Gly Phe Gly Pro His Gln Arg Leu
```

-continued

```
                   20                  25                  30
gag aag ctt gat tct ttg ctc tca gac tac gat att ctc tct tta tct    144
Glu Lys Leu Asp Ser Leu Leu Ser Asp Tyr Asp Ile Leu Ser Leu Ser
            35                  40                  45 aat atc cag cag cat tcg gta aga aaa aga gat cta cag act tca aca    192
Asn Ile Gln Gln His Ser Val Arg Lys Arg Asp Leu Gln Thr Ser Thr
    50                  55                  60 cat gta gaa aca cta cta act ttt tca gct ttg aaa agg cat ttt aaa    240
His Val Glu Thr Leu Leu Thr Phe Ser Ala Leu Lys Arg His Phe Lys
65                  70                  75                  80 tta tac ctg aca tca agt act gaa cgt ttt tca caa aat ttc aag gtc    288
Leu Tyr Leu Thr Ser Ser Thr Glu Arg Phe Ser Gln Asn Phe Lys Val
                85                  90                  95 gtg gtg gtg gat ggt aaa aac gaa agc gag tac act gta aaa tgg cag    336
Val Val Val Asp Gly Lys Asn Glu Ser Glu Tyr Thr Val Lys Trp Gln
            100                 105                 110 gac ttc ttc act gga cac gtg gtt ggt gag cct gac tct agg gtt cta    384
Asp Phe Phe Thr Gly His Val Val Gly Glu Pro Asp Ser Arg Val Leu
    115                 120                 125 gcc cac ata aga gat gat gat gtt ata atc aga atc aac aca gat ggg    432
Ala His Ile Arg Asp Asp Asp Val Ile Ile Arg Ile Asn Thr Asp Gly
130                 135                 140 gcc gaa tat aac ata gag cca ctt tgg aga ttt gtt aat gat acc aaa    480
Ala Glu Tyr Asn Ile Glu Pro Leu Trp Arg Phe Val Asn Asp Thr Lys
145                 150                 155                 160 gac aaa aga atg tta gtt tat aaa tct gaa gat atc aag aat gtt tca    528
Asp Lys Arg Met Leu Val Tyr Lys Ser Glu Asp Ile Lys Asn Val Ser
                165                 170                 175 cgt ttg cag tct cca aaa gtg tgt ggt tat tta aaa gtg gat aat gaa    576
Arg Leu Gln Ser Pro Lys Val Cys Gly Tyr Leu Lys Val Asp Asn Glu
            180                 185                 190 gag ttg ctc cca aaa ggg tta gta gac aga gaa cca cct gaa gag ctt    624
Glu Leu Leu Pro Lys Gly Leu Val Asp Arg Glu Pro Pro Glu Glu Leu
    195                 200                 205 gtt cat cga gtg aaa aga aga gct gac cca gat ccc atg aag aac acg    672
Val His Arg Val Lys Arg Arg Ala Asp Pro Asp Pro Met Lys Asn Thr
210                 215                 220 tgt aaa tta ttg gtg gta gca gat cat cgc ttc tac aga tac atg ggc    720
Cys Lys Leu Leu Val Val Ala Asp His Arg Phe Tyr Arg Tyr Met Gly
225                 230                 235                 240 aga ggg gaa gag agt aca act aca aat tac tta ata gag cta att gac    768
Arg Gly Glu Glu Ser Thr Thr Thr Asn Tyr Leu Ile Glu Leu Ile Asp
                245                 250                 255 aga gtt gat gac atc tat cgg aac act tca tgg gat aat gca ggt ttt    816
Arg Val Asp Asp Ile Tyr Arg Asn Thr Ser Trp Asp Asn Ala Gly Phe
            260                 265                 270 aaa ggc tat gga ata cag ata gag cag att cgc att ctc aag tct cca    864
Lys Gly Tyr Gly Ile Gln Ile Glu Gln Ile Arg Ile Leu Lys Ser Pro
    275                 280                 285 caa gag gta aaa cct ggt gaa aag cac tac aac atg gca aaa agt tac    912
Gln Glu Val Lys Pro Gly Glu Lys His Tyr Asn Met Ala Lys Ser Tyr
290                 295                 300 cca aat gaa gaa aag gat gct tgg gat gtg aag atg ttg cta gag caa    960
Pro Asn Glu Glu Lys Asp Ala Trp Asp Val Lys Met Leu Leu Glu Gln
305                 310                 315                 320 ttt agc ttt gat ata gct gag gaa gca tct aaa gtt gcc ttg gca cac    1008
Phe Ser Phe Asp Ile Ala Glu Glu Ala Ser Lys Val Cys Leu Ala His
                325                 330                 335 ctt ttc aca tac caa gat ttt gat atg gga act ctt gga tta gct tat    1056
```

```
                                          -continued

Leu Phe Thr Tyr Gln Asp Phe Asp Met Gly Thr Leu Gly Leu Ala Tyr
            340                 345                 350 gtt ggc tct ccc aga gca aac agc cat gga ggt gtt tgt cca aag gct      1104
Val Gly Ser Pro Arg Ala Asn Ser His Gly Gly Val Cys Pro Lys Ala
        355                 360                 365 tat tat agc cca gtt ggg aag aaa aat atc tat ttg aat agt ggt tgg      1152
Tyr Tyr Ser Pro Val Gly Lys Lys Asn Ile Tyr Leu Asn Ser Gly Leu
370                 375                 380 acg agc aca aag aat tat ggt aaa acc atc ctt aca aag gaa gct gac      1200
Thr Ser Thr Lys Asn Tyr Gly Lys Thr Ile Leu Thr Lys Glu Ala Asp
385                 390                 395                 400 ctg gtt aca act cat gaa ttg gga cat aat ttt gga gca gaa cat gat      1248
Leu Val Thr Thr His Glu Leu Gly His Asn Phe Gly Ala Glu His Asp
                405                 410                 415 ccg gat ggt cta gca gaa tgt gcc ccg aat gag gac cag gga ggg aaa      1296
Pro Asp Gly Leu Ala Glu Cys Ala Pro Asn Glu Asp Gln Gly Gly Lys
            420                 425                 430 tat gtc atg tat ccc ata gct gtg agt ggc gat cac gag aac aat aag      1344
Tyr Val Met Tyr Pro Ile Ala Val Ser Gly Asp His Glu Asn Asn Lys
        435                 440                 445 atg ttt tca aac tgc agt aaa caa tca atc tat aag acc att gaa agt      1392
Met Phe Ser Asn Cys Ser Lys Gln Ser Ile Tyr Lys Thr Ile Glu Ser
450                 455                 460 aag gcc cag gag tgt ttt caa gaa cga agc aat aaa gtt tgt ggg aac      1440
Lys Ala Gln Glu Cys Phe Gln Glu Arg Ser Asn Lys Val Cys Gly Asn
465                 470                 475                 480 tcg agg gtg gat gaa gga gaa gag tgt gat cct ggc atc atg tat ctg      1488
Ser Arg Val Asp Glu Gly Glu Glu Cys Asp Pro Gly Ile Met Tyr Leu
                485                 490                 495 aac aac gac acc tgc tgc aac agc gac tgc acg ttg aag gaa ggt gtc      1536
Asn Asn Asp Thr Cys Cys Asn Ser Asp Cys Thr Leu Lys Glu Gly Val
            500                 505                 510 cag tgc agt gac agg aac agt cct tgc tgt aaa aac tgt cag ttt gag      1584
Gln Cys Ser Asp Arg Asn Ser Pro Cys Cys Lys Asn Cys Gln Phe Glu
        515                 520                 525 act gcc cag aag aag tgc cag gag gcg att aat gct act tgc aaa ggc      1632
Thr Ala Gln Lys Lys Cys Gln Glu Ala Ile Asn Ala Thr Cys Lys Gly
530                 535                 540 gtg tcc tac tgc aca ggt aat agc agt gag tgc ccg cct cca gga aat      1680
Val Ser Tyr Cys Thr Gly Asn Ser Ser Glu Cys Pro Pro Pro Gly Asn
545                 550                 555                 560 gct gaa gat gac act gtt tgc ttg gat ctt ggc aag tgt aag gat ggg      1728
Ala Glu Asp Asp Thr Val Cys Leu Asp Leu Gly Lys Cys Lys Asp Gly
                565                 570                 575 aaa tgc atc cct ttc tgc gag agg gaa cag cag ctg gag tcc tgt gca      1776
Lys Cys Ile Pro Phe Cys Glu Arg Glu Gln Gln Leu Glu Ser Cys Ala
            580                 585                 590 tgt aat gaa act gac aac tcc tgc aag gtg tgc tgc agg gac ctt tcc      1824
Cys Asn Glu Thr Asp Asn Ser Cys Lys Val Cys Cys Arg Asp Leu Ser
        595                 600                 605 ggc cgc tgt gtg ccc tat gtc gat gct gaa caa aag aac tta ttt ttg      1872
Gly Arg Cys Val Pro Tyr Val Asp Ala Glu Gln Lys Asn Leu Phe Leu
610                 615                 620 agg aaa gga aag ccc tgt aca gta gga ttt tgt gac atg aat ggc aaa      1920
Arg Lys Gly Lys Pro Cys Thr Val Gly Phe Cys Asp Met Asn Gly Lys
625                 630                 635                 640 tgt gag aaa cga gta cag gat gta att gaa cga ttt tgg gat ttc att      1968
Cys Glu Lys Arg Val Gln Asp Val Ile Glu Arg Phe Trp Asp Phe Ile
                645                 650                 655
```

```
gac cag ctg agc atc aat act ttt gga aag ttt tta gca gac aac atc    2016
Asp Gln Leu Ser Ile Asn Thr Phe Gly Lys Phe Leu Ala Asp Asn Ile
        660                 665                 670 gtt ggg tct gtc ctg gtt ttc tcc ttg ata ttt tgg att cct ttc agc    2064
Val Gly Ser Val Leu Val Phe Ser Leu Ile Phe Trp Ile Pro Phe Ser
    675                 680                 685 att ctt gtc cat tgt gta acg tcg aaa tgc tga                        2097
Ile Leu Val His Cys Val Thr Ser Lys Cys
        690                 695

<210> SEQ ID NO 4
<211> LENGTH: 698
<212> TYPE: PRT
<213> ORGANISM: Homo sapiens

<400> SEQUENCE: 4

Met Arg Gln Ser Leu Leu Phe Leu Thr Ser Val Val Pro Phe Val Leu
 1               5                  10                  15

Ala Pro Arg Pro Pro Asp Asp Pro Gly Phe Gly Pro His Gln Arg Leu
            20                  25                  30

Glu Lys Leu Asp Ser Leu Leu Ser Asp Tyr Asp Ile Leu Ser Leu Ser
        35                  40                  45

Asn Ile Gln Gln His Ser Val Arg Lys Arg Asp Leu Gln Thr Ser Thr
    50                  55                  60

His Val Glu Thr Leu Leu Thr Phe Ser Ala Leu Lys Arg His Phe Lys
65                  70                  75                  80

Leu Tyr Leu Thr Ser Ser Thr Glu Arg Phe Ser Gln Asn Phe Lys Val
                85                  90                  95

Val Val Val Asp Gly Lys Asn Glu Ser Glu Tyr Thr Val Lys Trp Gln
            100                 105                 110

Asp Phe Phe Thr Gly His Val Val Gly Glu Pro Asp Ser Arg Val Leu
        115                 120                 125

Ala His Ile Arg Asp Asp Val Ile Ile Arg Ile Asn Thr Asp Gly
    130                 135                 140

Ala Glu Tyr Asn Ile Glu Pro Leu Trp Arg Phe Val Asn Asp Thr Lys
145                 150                 155                 160

Asp Lys Arg Met Leu Val Tyr Lys Ser Glu Asp Ile Lys Asn Val Ser
                165                 170                 175

Arg Leu Gln Ser Pro Lys Val Cys Gly Tyr Leu Lys Val Asp Asn Glu
            180                 185                 190

Glu Leu Leu Pro Lys Gly Leu Val Asp Arg Glu Pro Pro Glu Glu Leu
        195                 200                 205

Val His Arg Val Lys Arg Arg Ala Asp Pro Asp Pro Met Lys Asn Thr
    210                 215                 220

Cys Lys Leu Leu Val Val Ala Asp His Arg Phe Tyr Arg Tyr Met Gly
225                 230                 235                 240

Arg Gly Glu Glu Ser Thr Thr Thr Asn Tyr Leu Ile Glu Leu Ile Asp
                245                 250                 255

Arg Val Asp Asp Ile Tyr Arg Asn Thr Ser Trp Asp Asn Ala Gly Phe
            260                 265                 270

Lys Gly Tyr Gly Ile Gln Ile Glu Gln Ile Arg Ile Leu Lys Ser Pro
        275                 280                 285

Gln Glu Val Lys Pro Gly Glu Lys His Tyr Asn Met Ala Lys Ser Tyr
    290                 295                 300

Pro Asn Glu Glu Lys Asp Ala Trp Asp Val Lys Met Leu Leu Glu Gln
305                 310                 315                 320
```

-continued

```
Phe Ser Phe Asp Ile Ala Glu Glu Ala Ser Lys Val Cys Leu Ala His
            325                 330                 335

Leu Phe Thr Tyr Gln Asp Phe Asp Met Gly Thr Leu Gly Leu Ala Tyr
            340                 345                 350

Val Gly Ser Pro Arg Ala Asn Ser His Gly Gly Val Cys Pro Lys Ala
            355                 360                 365

Tyr Tyr Ser Pro Val Gly Lys Lys Asn Ile Tyr Leu Asn Ser Gly Leu
370                 375                 380

Thr Ser Thr Lys Asn Tyr Gly Lys Thr Ile Leu Thr Lys Glu Ala Asp
385                 390                 395                 400

Leu Val Thr Thr His Glu Leu Gly His Asn Phe Gly Ala Glu His Asp
            405                 410                 415

Pro Asp Gly Leu Ala Glu Cys Ala Pro Asn Glu Asp Gln Gly Gly Lys
            420                 425                 430

Tyr Val Met Tyr Pro Ile Ala Val Ser Gly Asp His Glu Asn Asn Lys
            435                 440                 445

Met Phe Ser Asn Cys Ser Lys Gln Ser Ile Tyr Lys Thr Ile Glu Ser
    450                 455                 460

Lys Ala Gln Glu Cys Phe Gln Glu Arg Ser Asn Lys Val Cys Gly Asn
465                 470                 475                 480

Ser Arg Val Asp Glu Gly Glu Glu Cys Asp Pro Gly Ile Met Tyr Leu
            485                 490                 495

Asn Asn Asp Thr Cys Cys Asn Ser Asp Cys Thr Leu Lys Glu Gly Val
            500                 505                 510

Gln Cys Ser Asp Arg Asn Ser Pro Cys Cys Lys Asn Cys Gln Phe Glu
            515                 520                 525

Thr Ala Gln Lys Lys Cys Gln Glu Ala Ile Asn Ala Thr Cys Lys Gly
            530                 535                 540

Val Ser Tyr Cys Thr Gly Asn Ser Ser Glu Cys Pro Pro Gly Asn
545                 550                 555                 560

Ala Glu Asp Asp Thr Val Cys Leu Asp Leu Gly Lys Cys Lys Asp Gly
            565                 570                 575

Lys Cys Ile Pro Phe Cys Glu Arg Glu Gln Gln Leu Glu Ser Cys Ala
            580                 585                 590

Cys Asn Glu Thr Asp Asn Ser Cys Lys Val Cys Arg Asp Leu Ser
            595                 600                 605

Gly Arg Cys Val Pro Tyr Val Asp Ala Glu Gln Lys Asn Leu Phe Leu
610                 615                 620

Arg Lys Gly Lys Pro Cys Thr Val Gly Phe Cys Asp Met Asn Gly Lys
625                 630                 635                 640

Cys Glu Lys Arg Val Gln Asp Val Ile Glu Arg Phe Trp Asp Phe Ile
            645                 650                 655

Asp Gln Leu Ser Ile Asn Thr Phe Gly Lys Phe Leu Ala Asp Asn Ile
            660                 665                 670

Val Gly Ser Val Leu Val Phe Ser Leu Ile Phe Trp Ile Pro Phe Ser
            675                 680                 685

Ile Leu Val His Cys Val Thr Ser Lys Cys
            690                 695

<210> SEQ ID NO 5
<211> LENGTH: 8
<212> TYPE: PRT
<213> ORGANISM: Homo sapiens
```

```
-continued

<400> SEQUENCE: 5

Leu Ala Gln Ala Val Arg Ser Ser
 1               5

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: mixed
      oligonucleotide primer
<220> FEATURE:
<221> NAME/KEY: unsure
<222> LOCATION: (9)
<223> OTHER INFORMATION: unsure

<400> SEQUENCE: 6
aartaygtna tgtaycc                                                17

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: mixed
      oligonucleotide primer

<400> SEQUENCE: 7
ccrcartcrc aytcytc                                                17

<210> SEQ ID NO 8
<211> LENGTH: 6
<212> TYPE: PRT
<213> ORGANISM: Homo sapiens

<400> SEQUENCE: 8

Glu Glu Cys Asp Cys Gly
 1               5

<210> SEQ ID NO 9
<211> LENGTH: 11
<212> TYPE: PRT
<213> ORGANISM: Homo sapiens

<400> SEQUENCE: 9

Ile Ala Val Ser Gly Asp His Glu Asn Asn Lys
 1               5                  10
```

ANTIBODIES THAT BIND TNF-α CONVERTING ENZYME

This application is a divisional application of U.S. Ser. No. 09/726,968 filed 29 Nov. 2000, and issued as U.S. Pat. No. 6,555,354; which is a divisional application of U.S. Ser. No. 09/579,766, filed 26 May 2000 and issued as U.S. Pat. No. 6,406,901; which was a divisional application of U.S. Ser. No. 09/440,324, filed 15 Nov. 1999, now abandoned; which was a continuation application of U.S. Ser. No. 09/183,275, filed 30 Oct. 1998 and issued as U.S. Pat. No. 6,013,466; which was a continuation application of U.S. Ser. No. 08/655,345, filed 23 May 1996 and issued as U.S. Pat. No. 5,830,742; which claimed the priority of provisional applications U.S. Ser. No. 60/033,750, filed 20 Jul. 1995, and U.S. Ser. No. 60/033,169, filed 08 Jun. 1995; all of which are incorporated by reference herein.

FIELD OF THE INVENTION

The invention is directed to purified and isolated TNF-α converting enzyme, the nucleic acids encoding such enzyme, processes for production of recombinant TNF-α convertases, pharmaceutical compositions containing such enzymes, and their use in various assays and therapies.

BACKGROUND OF THE INVENTION

Tumor necrosis factor-α (TNF-α, also known as cachectin) is a mammalian protein capable of inducing a variety of effects on numerous cell types. TNF-α was initially characterized by its ability to cause lysis of tumor cells and is produced by activated cells such as mononuclear phagocytes, T-cells, B-cells, mast cells and NK cells. There are two forms of TNF-α, a type II membrane protein of relative molecular mass 26,000 (26 kD) and a soluble 17 kD form generated from the cell-bound protein by proteolytic cleavage. TNF-α is a principal mediator of the host response to gram-negative bacteria. Lipopolysaccharide (LPS, also called endotoxin), derived from the cell wall of gram-negative bacteria, is a potent stimulator of TNF-α synthesis. Because the deleterious effects which can result from an over-production or an unregulated-production of TNF-α are extremely serious, considerable efforts have been made to control or regulate the serum level of TNF-α. An important part in the effort to effectively control serum TNF-α levels is the understanding of the mechanism of TNF-α biosynthesis.

The mechanism by which TNF-α is secreted has not previously been elucidated. Kriegler et al. *Cell*, 53:45 (1988) conjectured that TNF-α "secretion" is due to the converting of the 26 kD membrane-bound molecule by a then unknown proteolytic enzyme or protease. Scuderi et. al., *J. Immunology*, 143:168 (1989), suggested that the release of TNF-α from human leukocyte cells is dependent on one or more serine proteases, e.g., a leukocyte elastase or trypsin. A serine protease inhibitor, p-toluenesulfonyl-L-arginine methyl ester, was found to suppress human leukocyte TNF-α release in a concentration-dependent manner. Scuderi et. al. suggested that an arginine methyl ester competes for the arginine-binding site in the enzyme's reactive center and thereby blocks hydrolysis. The lysine and phenylalanine analogs of the inhibitor reportedly failed to mimic the arginine methyl ester. However, it was never shown that this compound acted by inhibiting a protease that cleaves the 26 kD TNF. More recently, it has been reported that metalloprotease inhibitors block the release of TNF from THP-1 cells. See Mohler et al., *Nature* 370:218 (1994); Gearing et al., *Nature*, 370:555 (1994); and McGeehan et al., *Nature*, 370:568 (1994).

Most, but not all, proteases recognize a specific amino acid sequence. Some proteases primarily recognize residues located N-terminal of the cleaved bond, some recognize residues located C-terminal of the cleaved bond, and some proteases recognize residues on both sides of the cleaved bond. Metalloprotease enzymes utilize a bound metal ion, generally $Zn^{2+}$, to catalyze the hydrolysis of the peptide bond. Metalloproteases are implicated in joint destruction (the matrix metalloproteases), blood pressure regulation (angiotensin converting enzyme), and regulation of peptide-hormone levels (neutral endopeptidase-24.11).

SUMMARY OF THE INVENTION

The invention pertains to biologically active TNF-α converting enzyme ("TACE") as an isolated and purified polypeptide. In addition, the invention is directed to isolated nucleic acids encoding TACE and to expression vectors comprising a cDNA encoding TACE. Within the scope of this invention are host cells that have been transfected or transformed with expression vectors that comprise a cDNA encoding TACE, and processes for producing TACE by culturing such host cells under conditions conducive to expression of TACE. By virtue of the purification of TACE, antibodies, and in particular, monoclonal antibodies against TACE are an aspect of the invention. In addition, assays utilizing TACE to screen for potential inhibitors thereof, and methods of using TACE as a therapeutic agent for the treatment of diseases mediated by cell-bound TNF-α or other molecules are encompassed by the invention. Further, methods of using TACE in the design of inhibitors thereof are also an aspect of the invention.

The isolated and purified metalloprotease of the invention is capable of converting TNF-α from the 26 kD membrane-bound form to the 17 kD form, and which has a molecular weight of between approximately 66 kD and approximately 97 kD. The cDNA sequence of TACE is shown in SEQ ID NO:1. The isolated and purified TNF-α converting enzyme ("TACE") comprises amino acids 18–824 of SEQ ID NO:2.

Inhibition of the TACE inhibits release of TNF-α into the serum and other extracellular spaces. TACE inhibitors would therefore have clinical utility in treating conditions characterized by over-production or upregulated production of TNF-α. A particularly useful TACE inhibitor for certain pathological conditions would selectively inhibit TACE while not affecting TNF-β (also known as lymphotoxin) serum levels. The over-production or unregulated production of TNF-α has been implicated in certain conditions and diseases, for example, Systemic Inflammatory Response Syndrome, reperfusion injury, cardiovascular disease, infectious disease such as HIV infection and HIV neuropathy, obstetrical or gynecological disorders, inflammatory disease/auto-immunity, allergic/atopic diseases, malignancy, transplants including organ transplant rejection or graft-versus-host disease, cachexia, congenital, dermatologic, neurologic, renal, toxicity, and metabolic/idiopathic diseases.

Inhibitors of TACE would prevent the cleavage of cell-bound TNF-α thereby reducing the level of TNF-α in serum and tissues. The present invention encompasses such an embodiment and comprises a method of inhibiting the cleavage of TNF-α from cell membranes in a mammal comprising administering to such mammal an effective amount of a compound that inhibits the TNF-α proteolytic activity of an enzyme comprising the sequence of amino acids from 18 to 671 through 824 of SEQ ID NO:2. In addition, the invention comprises a method for treating a mammal having a disease characterized by an overproduction or an upregulated production of TNF-α, comprising administering to the mammal a composition comprising an effective amount of a compound that inhibits the TNF-α proteolytic activity of an enzyme comprising the sequence of amino acids 18–824 of SEQ ID NO:2. Such inhibitors would be of significant clinical utility and could be potential therapeutics for treating the above-listed TNF-α-related disorders. Isolation and purification of TACE would provide a significant advancement in the effort to develop inhibitors of such enzyme, and the treatment of TNF-associated diseases, and indeed, could lead to use of TACE itself as a therapeutic agent for certain physiological disorders. For example, in addition to TNF-α, other cytokines as well as cytokine receptors and several adhesion proteins may be released from the cell surface by TACE or related proteases. TACE may be administered to modulate or remove cell surface cytokines, cytokine receptors and adhesion proteins involved in tumor cell growth, inflammation, or fertilization.

DETAILED DESCRIPTION OF THE INVENTION

A cDNA encoding human TNF-α converting enzyme ("TACE") has been isolated and is disclosed in SEQ ID NO:1. This discovery of the cDNA encoding human TACE enables construction of expression vectors comprising nucleic acid sequences encoding TACE; host cells transfected or transformed with the expression vectors; biologically active human TACE as isolated and purified proteins; and antibodies immunoreactive with TACE.

Isolated and purified TACE polypeptides according to the invention are useful for detecting the TACE-inhibiting activity of a molecule. In such a method involving routine and conventional techniques, a molecule of unknown TACE-inhibiting activity is mixed with a substrate and incubated with a TACE polypeptide. The extent of substrate cleavage then can be determined chromatographically.

In addition, TACE polypeptides according to the invention are useful for the structure-based design of a TACE inhibitor. Such a design would comprise the steps of determining the three-dimensional structure of such TACE polypeptide, analyzing the three-dimensional structure for the likely binding sites of substrates, synthesizing a molecule that incorporates a predictive reactive site, and determining the TACE-inhibiting activity of the molecule.

Antibodies immunoreactive with TACE, and in particular, monoclonal antibodies against TACE, are now made available through the invention. Such antibodies may be useful for inhibiting TACE activity in vivo and for detecting the presence of TACE in a sample.

As used herein, the term "TACE" refers to a genus of polypeptides that are capable of converting the 26 kD cell membrane-bound form of TNF-α (that includes an intracellular region, a membrane region, and an extracellular region), into the soluble 17 kD form that comprises the C-terminal 156 residues of the TNF-α protein. TACE encompasses proteins having the amino acid sequence 18 to 824 of SEQ ID NO:2, as well as those proteins having a high degree of similarity (at least 80%, and more preferably 90% homology) with the amino acid sequence 18 to 824 of SEQ ID NO:2 and which proteins are biologically active. In addition, TACE refers to the biologically active gene products of the nucleotides 52–2472 of SEQ ID NO: 1. Further encompassed by the term "TACE" are the membrane-bound proteins (which include an intracellular region, a membrane region, and an extracellular region), and soluble or truncated proteins which comprise primarily the extracellular portion of the protein, retain biological activity and are capable of being secreted. Specific examples of such soluble proteins are those comprising the sequence of amino acids 18–671 of SEQ ID NO:2. Truncated versions are those having less than the extracellular portion of the protein and comprise, for example, amino acids 18–477 of SEQ ID NO:2, or that comprise substantially all of the catalytic domain, i.e., amino acids 215 to 477 of SEQ ID NO:2.

The isolated and purified TACE according to the invention has a molecular weight between about 66 kD and about 97 kD as determined by SDS-polyacrylamide gel electrophoresis (SDS-PAGE). More specifically, TACE was found to have a molecular weight of approximately 80 kD as determined by SDS-PAGE.

The term "isolated and purified" as used herein, means that TACE is essentially free of association with other proteins or polypeptides, for example, as a purification product of recombinant host cell culture or as a purified product from a non-recombinant source. The term "substantially purified" as used herein, refers to a mixture that contains TACE and is essentially free of association with other proteins or polypeptides, but for the presence of known proteins that can be removed using a specific antibody, and which substantially purified TACE retains biological activity. The term "purified TACE" refers to either the "isolated and purified" form of TACE or the "substantially purified" form of TACE, as both are described herein.

The term "biologically active" as it refers to TACE, means that the TACE is capable of converting the 26 kD cell form of TNF-α into the 17 kD form.

A "nucleotide sequence" refers to a polynucleotide molecule in the form of a separate fragment or as a component of a larger nucleic acid construct, that has been derived from DNA or RNA isolated at least once in substantially pure form (i.e., free of contaminating endogenous materials) and in a quantity or concentration enabling identification, manipulation, and recovery of its component nucleotide sequences by standard biochemical methods (such as those outlined in Sambrook et al., *Molecular Cloning. A Laboratory Manual*, 2nd ed., Cold Spring Harbor Laboratory, Cold Spring Harbor, N.Y. (1989)). Such sequences are preferably provided in the form of an open reading frame uninterrupted by internal non-translated sequences, or introns, that are typically present in eukaryotic genes. Sequences of non-translated DNA may be present 5' or 3' from an open reading frame, where the same do not interfere with manipulation or expression of the coding region.

A "TACE variant" as referred to herein, means a polypeptide substantially homologous to native TACE, but which has an amino acid sequence different from that of native TACE (human, murine or other mammalian species) because of one or more deletions, insertions or substitutions. The variant amino acid sequence preferably is at least 80% identical to a native TACE amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Variants may comprise conservatively substituted sequences, meaning that a given amino acid residue is replaced by a residue having similar physiochemical characteristics. Conservative substitutions are well known in the art and include substitution of one aliphatic residue for another, such as Ile, Val, Leu, or Ala for one another, or substitutions of one polar residue for another, such as between Lys and Arg; Glu and Asp; or Gln and Asn. Conventional procedures and methods can be used for making and using such variants. Other such conservative substitutions, for example, substitutions of entire regions having similar hydrophobicity characteristics, are well known and routinely performed. Naturally occurring TACE variants are also encompassed by the invention. Examples of such variants are proteins that result from alternate mRNA splicing events or from proteolytic cleavage of the TACE protein, wherein the TACE proteolytic property is retained. Alternate splicing of mRNA may yield a truncated but biologically active TACE protein, such as a naturally occurring soluble form of the protein, for example, as shown in -SEQ ID NO:4. Variations attributable to proteolysis include, for example, differences in the N- or C-termini upon expression in different types of host cells, due to proteolytic removal of one or more terminal amino acids from the TACE protein (generally from 1–5 terminal amino acids).

As stated above, the invention provides isolated and purified, or homogeneous, TACE polypeptides, both recombinant and non-recombinant. Variants and derivatives of native TACE proteins that retain the desired biological activity may be obtained by mutations of nucleotide sequences coding for native TACE polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques, January* 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462 all of which are incorporated by reference.

TACE may be modified to create TACE derivatives by forming covalent or aggregative conjugates with other chemical moieties, such as glycosyl groups, polyethylene glycol (PEG) groups, lipids, phosphate, acetyl groups and the like. Covalent derivatives of TACE may be prepared by linking the chemical moieties to functional groups on TACE amino acid side chains or at the N-terminus or C-terminus of a TACE polypeptide or the extracellular domain thereof. Other derivatives of TACE within the scope of this invention include covalent or aggregative conjugates of TACE or its fragments with other proteins or polypeptides, such as by synthesis in recombinant culture as N-terminal or C-terminal fusions. For example, the conjugate may comprise a signal or leader polypeptide sequence (e.g. the α-factor leader of *Saccharomyces*) at the N-terminus of a TACE polypeptide. The signal or leader peptide co-translationally or post-translationally directs transfer of the conjugate from its site of synthesis to a site inside or outside of the cell membrane or cell wall.

TACE polypeptide conjugates can comprise peptides added to facilitate purification and identification of TACE. Such peptides include, for example, poly-His or the antigenic identification peptides described in U.S. Pat. No. 5,011,912 and in Hopp et al., *Bio/Technology* 6:1204, 1988.

The invention further includes TACE polypeptides with or without associated native-pattern glycosylation. TACE expressed in yeast or mammalian expression systems (e.g., COS-7 cells) may be similar to or significantly different from a native TACE polypeptide in molecular weight and glycosylation pattern, depending upon the choice of expression system. Expression of TACE polypeptides in bacterial expression systems, such as *E. coli*, provides non-glycosylated molecules. Glycosyl groups may be removed through conventional methods, in particular those utilizing glycopeptidase. In general, glycosylated TACE may be incubated with a molar excess of glycopeptidase (Boehringer Mannheim).

Equivalent DNA constructs that encode various additions or substitutions of amino acid residues or sequences, or deletions of terminal or internal residues or sequences not needed for biological activity are encompassed by the invention. For example, N-glycosylation sites in the TACE extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Nucleic acid sequences within the scope of the invention include isolated DNA and RNA sequences that hybridize to the native TACE nucleotide sequences disclosed herein under conditions of moderate or high stringency, and which encode biologically active TACE. Conditions of moderate stringency, as known to those having ordinary skill in the art, and as defined by Sambrook et al. *Molecular Cloning: A Laboratory Manual*, 2 ed. Vol. 1, pp. 1.101–104, Cold Spring Harbor Laboratory Press, (1989), include use of a prewashing solution of 5×SSC, 0.5% SDS, 1.0 mM EDTA (pH 8.0) and hybridization conditions of about 50° C.–60° C., 5×SSC, overnight, preferably 55° C. Conditions of high stringency include higher temperatures of hybridization and washing. The skilled artisan will recognize that the temperature and wash solution salt concentration may be adjusted as necessary according to factors such as the length of the probe.

Due to the known degeneracy of the genetic code wherein more than one codon can encode the same amino acid, a DNA sequence may vary from that shown in SEQ ID NO:1 and still encode a TACE protein having the amino acid sequence of SEQ ID NO:2. Such variant DNA sequences may result from silent mutations (e.g., occurring during PCR amplification), or may be the product of deliberate mutagenesis of a native sequence.

The invention thus provides equivalent isolated DNA sequences encoding biologically active TACE, selected from: (a) the coding region of a native mammalian TACE gene; (b) cDNA comprising the nucleotide sequence presented in SEQ ID NO:1; (c) DNA capable of hybridization to a DNA of (a) under moderately stringent conditions and which encodes biologically active TACE; and (d) DNA which is degenerate as a result of the genetic code to a DNA defined in (a), (b) or (c) and which encodes biologically active TACE. TACE proteins encoded by such DNA equivalent sequences are encompassed by the invention.

DNA that are equivalents to the DNA sequence of SEQ ID NO:1 will hybridize under moderately stringent or highly stringent conditions to the double-stranded native DNA sequence that encode polypeptides comprising amino acid sequences of 18—Xaa of SEQ ID NO:2, wherein Xaa is an amino acid from 671 to 824. Examples of TACE proteins encoded by such DNA, include, but are not limited to, TACE fragments (soluble or membrane-bound) and TACE proteins comprising inactivated N-glycosylation site(s), inactivated KEX2 protease processing site(s), or conservative amino acid substitution(s), as described above. TACE proteins encoded by DNA derived from other mammalian species, wherein the DNA will hybridize under conditions of moderate or high stringency to the complement of the cDNA of SEQ ID NO:1 are also encompassed.

Alternatively, TACE-binding proteins, such as the anti-TACE antibodies of the invention, can be bound to a solid phase such as a column chromatography matrix or a similar substrate suitable for identifying, separating or purifying cells that express the TACE on their surface. Adherence of TACE-binding proteins to a solid phase contacting surface can be accomplished by any means, for example, magnetic microspheres can be coated with TACE-binding proteins and held in the incubation vessel through a magnetic field. Suspensions of cell mixtures are contacted with the solid phase that has TACE-binding proteins thereon. Cells having TACE on their surface bind to the fixed TACE-binding protein and unbound cells then are washed away. This affinity-binding method is useful for purifying, screening or separating such TACE-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing TACE-expressing cells first can be incubated with a biotinylated TACE-binding protein. Incubation periods are typically at least one hour in duration to ensure sufficient binding to TACE. The resulting mixture then is passed through a column packed with avidin-coated beads, whereby the high affinity of biotin for avidin provides the binding of the TACE-binding cells to the beads. Use of avidin-coated beads is known in the art. See Berenson, et al. *J. Cell. Biochem.*, 10D:239 (1986). Wash of unbound material and the release of the bound cells is performed using conventional methods.

In the methods described above, suitable TACE-binding proteins are anti-TACE antibodies, and other proteins that are capable of high-affinity binding of TACE. A preferred TACE-binding protein is an anti-TACE monoclonal antibody obtained, for example, as described in Example 4.

TACE polypeptides may exist as oligomers, such as covalently-linked or non-covalently-linked dimers or trimers. Oligomers may be linked by disulfide bonds formed between cysteine residues on different TACE polypeptides. In one embodiment of the invention, a TACE dimer is created by fusing TACE to the Fc region of an antibody (e.g., IgG1) in a manner that does not interfere with biological activity of TACE. The Fc polypeptide preferably is fused to the C-terminus of a soluble TACE (comprising only the extracellular domain). General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the TACE:Fc fusion protein is inserted into an appropriate expression vector. TACE:Fc fusion proteins are allowed to assemble much like antibody molecules, whereupon interchain disulfide bonds form between Fc polypeptides, yielding divalent TACE. If fusion proteins are made with both heavy and light chains of an antibody, it is possible to form a TACE oligomer with as many as four TACE extracellular regions. Alternatively, one can link two soluble TACE domains with a peptide linker.

Recombinant expression vectors containing a nucleic acid sequence encoding TACE can be prepared using well known methods. The expression vectors include a TACE DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the TACE DNA sequence. Thus, a promoter nucleotide sequence is operably linked to a TACE DNA sequence if the promoter nucleotide sequence controls the transcription of the TACE DNA sequence. The ability to replicate in the desired host cells, usually conferred by an origin of replication, and a selection gene by which transformants are identified, may additionally be incorporated into the expression vector.

In addition, sequences encoding appropriate signal peptides that are not naturally associated with TACE can be incorporated into expression vectors. For example, a DNA sequence for a signal peptide (secretory leader) may be fused in-frame to the TACE sequence so that TACE is initially translated as a fusion protein comprising the signal peptide. A signal peptide that is functional in the intended host cells enhances extracellular secretion of the TACE polypeptide. The signal peptide may be cleaved from the TACE polypeptide upon secretion of TACE from the cell.

Suitable host cells for expression of TACE polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce TACE polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a TACE polypeptide may include an N-terminal methionine residue to facilitate expression of the recombinant polypeptide in the prokaryotic host cell. The N-terminal Met may be cleaved from the expressed recombinant TACE polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct en expression vector using pBR322, an appropriate promoter and a TACE DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9 (ATCC 37092)) and pPLc28 (resident in *E. coli* RR1 (ATCC 53082)).

TACE polypeptides alternatively may be expressed in yeast host cells, preferably from the *Saccharomyces* genus (e.g., *S. cerevisiae*). Other genera of yeast, such as *Pichia, K. lactis* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene*, 107:285–195 (1991); and van den Berg et. al., *Bio/Technology*, 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* ($Amp^r$ gene and origin of replication) into the above-described yeast vectors.

The yeast α-factor leader sequence may be employed to direct secretion of a TACE polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U. S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant TACE polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. The vectors may be derived from retroviruses. In place of the native signal sequence, a heterologous signal sequence may be added, such as the signal sequence for IL-7 described in U.S. Pat. No. 4,965,195; the signal sequence for IL-2 receptor described in Cosman et al., *Nature* 312:768 (1984); the IL-4 signal peptide described in EP 367,566; the type I IL-1 receptor signal peptide described in U.S. Pat. No. 4,968,607; and the type II IL-1 receptor signal peptide described in EP 460,846.

An isolated and purified TACE protein according to the invention may be produced by recombinant expression systems as described above or purified from naturally occurring cells. TACE can be substantially purified, as indicated by a single protein band upon analysis by SDS-polyacrylamide gel electrophoresis (SDS-PAGE). One process for producing TACE comprises culturing a host cell transformed with an expression vector comprising a DNA sequence that encodes TACE under conditions sufficient to promote expression of TACE. TACE is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium. For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify TACE. Some or all of the foregoing purification steps, in various combinations, are well known and can be employed to provide an isolated and purified recombinant protein.

In addition to recombinantly producing TACE, TACE may be isolated and purified from an activated monocytic cell line, THP-1. THP-1 cells typically produce more TNF-α than do HL-60 cells, and are a preferred source for TACE. Other sources for TACE may be used, and TACE may also be found in other types of cells that produce TNF-α. Once a source for TACE is identified, TACE may be isolated and purified by first optionally stimulating the source cells to produce TNF-α. Stimulation may not be necessary, however, it can be done using techniques that are well-known in the art. The cells are then harvested, washed, and plasma membranes isolated according to conventional procedures. A particularly preferred method of isolating the plasma membranes is method number three as described in Maeda et. al., *Biochim. et. Biophys. Acta*, 731:115 (1983); except that dithiothreitol should not be included in this method since it was determined that dithiothreitol blocks TACE activity. Proteins from the cell membrane then can be solubilized by suspending the membrane preparation in a dilute solution of non-ionic detergent, followed by brief homogenization. Phospholipids then can be extracted using conventional methods.

It is possible to utilize an affinity column comprising a TACE-binding protein to affinity-purify expressed TACE polypeptides. TACE polypeptides can be removed from an affinity column using conventional techniques, e.g., in a high salt elution buffer and then dialyzed into a lower salt buffer for use or by changing pH or other components depending on the affinity matrix utilized. Example 4 describes a procedure for employing TACE of the invention to generate monoclonal antibodies directed against TACE.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-FIPLC can be employed for final purification steps. Microbial cells can be disrupted by any convenient method, including freeze-thaw cycling, sonication, mechanical disruption, or use of cell lysing agents.

Transformed yeast host cells are preferably employed to express TACE as a secreted polypeptide in order to simplify purification. Secreted recombinant polypeptide from a yeast host ell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Antisense or sense oligonucleotides comprising a single-stranded nucleic acid sequence (either RNA or DNA) capable of binding to a target TACE mRNA sequence (forming a duplex) or to the TACE sequence in the double-stranded DNA helix (forming a triple helix) can be made according to the invention. Antisense or sense oligonucleotides, according to the present invention, comprise a fragment of the coding region of TACE cDNA. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of complexes that block translation (RNA) or transcription (DNA) by one of several means, including enhanced degradation of the duplexes, premature termination of transcription or translation, or by other means. The antisense oligonucleotides thus may be used to block expression of TACE proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Isolated and purified TACE or a fragment thereof, and in particular, the extracellular domain of TACE, may also be useful itself as a therapeutic agent in regulating the levels of certain cell surface proteins. In addition to TNF-α, other cytokines as well as cytokine receptors and several adhesion proteins may be released from the cell surface by TACE or related proteases. TACE or a fragment thereof, in particular, the extracellular domain of TACE, may be administered to modulate or remove cell surface cytokines, cytokine receptors and adhesion proteins involved in tumor cell growth, inflammation, or fertilization. When used as a therapeutic agent, TACE can be formulated into pharmaceutical compositions according to known methods. TACE can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain TACE complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of TACE.

TACE may be assayed using any of a variety of metalloprotease assays known in the art. In general, TACE can be assayed through the use of a peptide substrate that represents the natural cleavage site of TNF-α. For example, in order to detect the cleavage of a substrate by TACE, the substrate can be tagged with a fluorescent group on one side of the cleavage site and with a fluorescence-quenching group on the opposite side of the cleavage site. Upon cleavage by TACE, quenching is eliminated thus providing a detectable signal. Alternatively, the substrate may be tagged with a colorimetric leaving group that more strongly absorbs upon cleavage. Alternatively, the substrate may have a thioester group synthesized into the cleavage site of the substrate so that upon cleavage by TACE, the thiol group remains and can be easily detected using conventional methods. A particularly preferred method of detecting TACE activity in a sample is described in Example 1, infra. Other methods of detecting TACE activity may be utilized without resorting to undue experimentation.

As further described in Example 1, infra, a quantitative assay for TACE also may be used which assay involves incubating the peptide substrate, at about 1 mM, with TACE at 37° C. for a fixed period of time; stopping the reaction by the addition of an acid or a metal chelator; and determining the extent of cleavage by HPLC analysis.

Within an aspect of the invention, TACE, and peptides based on the amino acid sequence of TACE, may be utilized to prepare antibodies that specifically bind to TACE. A specific example of such antibody preparation is described in Example 4 herein. The term "antibodies" is meant to include polyclonal antibodies, monoclonal antibodies, fragments thereof such as F(ab')2, and Fab fragments, as well as any recombinantly produced binding partners. Antibodies are defined to be specifically binding if they bind TACE with a $K_a$ of greater than or equal to about $10^7 M^{-1}$. Affinities of binding partners or antibodies can be readily determined using conventional techniques, for example those described by Scatchard et al., *Ann. N.Y. Acad. Sci.*, 51:660 (1949).

Polyclonal antibodies can be readily generated from a variety of sources, for example, horses, cows, goats, sheep, dogs, chickens, rabbits, mice or rats, using procedures that are well-known in the art. In general, purified TACE, or a peptide based on the amino acid sequence of TACE that is appropriately conjugated, is administered to the host animal typically through parenteral injection. The immunogenicity of TACE may be enhanced through the use of an adjuvant, for example, Freund's complete or incomplete adjuvant. Following booster immunizations, small samples of serum are collected and tested for reactivity to TACE or the TACE peptides. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay, radio-immunoprecipitation, enzyme-linked immuno-sorbent assays (ELISA), dot blot assays, and sandwich assays, see U.S. Pat. Nos. 4,376,110 and 4,486,530.

Monoclonal antibodies may be readily prepared using well-known procedures, see for example, the procedures described in U.S. Pat. Nos. RE 32,011, 4,902,614, 4,543,439 and 4,411,993; Monoclonal Antibodies, Hybridomas: *A New Dimension in Biological Analyses*, Plenum Press, Kennett, McKearn, and Bechtol (eds.), 1980. Briefly, the host animals, such as mice are injected intraperitoneally at least once, and preferably at least twice at about 3 week intervals with isolated and purified TACE or conjugated TACE peptide, optionally in the presence of adjuvant. Mouse sera are then assayed by conventional dot blot technique or antibody capture (ABC) to determine which animal is best to fuse. Approximately two to three weeks later, the mice are given an intravenous boost of TACE or conjugated TACE peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as, $^{125}$I-TACE is added to each well followed by incubation. Positive wells can be subsequently detected by autoradiography. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3:1–9 (1990) which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7:394 (1989).

Other types of "antibodies" may be produced using the information provided herein in conjunction with the state of knowledge in the art. For example, humanized antibodies that are capable of specifically binding TACE are also encompassed by the invention.

Once isolated and purified, the antibodies against TACE may be used to detect the presence of TACE in a sample using established assay protocols. Further, the antibodies of the invention may be used therapeutically to bind to TACE and inhibit its activity in vivo.

The purified TACE according to the invention will facilitate the discovery of inhibitors of TACE, and thus, inhibitors of excessive TNF-α release. The use of a purified TACE polypeptide in the screening of potential inhibitors thereof is important and can virtually eliminate the possibility of interfering reactions with contaminants. Such a screening assay for detecting the TACE-inhibiting activity of a molecule would typically involve mixing the potential inhibitor molecule with an appropriate substrate, incubating TACE that is at least substantially purified with the mixture, and determining the extent of substrate cleavage as, for example, described above. While various appropriate substrates may be designed for use in the assay, preferably, a peptidyl substrate is used, and which substrate comprises the amino acid sequence Leu-Ala-Gln-Ala-Val-Arg-Ser-Ser (SEQ ID NO:5).

In addition, TACE polypeptides can also be used for structure-based design of TACE-inhibitors. Such structure-based design is also known as "rational drug design." The TACE polypeptides can be three-dimensionally analyzed by, for example, X-ray crystallography, nuclear magnetic resonance or homology modeling, all of which are well-known methods. The use of TACE structural information in molecular modeling software systems to assist in inhibitor design and inhibitor-TACE interaction is also encompassed by the invention. Such computer-assisted modeling and drug design may utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively-charged moiety to which is attached a series of other groups designed to fit the specificity pockets of the particular protease. A particular method of the invention comprises analyzing the three dimensional structure of TACE for likely binding sites of substrates, synthesizing a new molecule that incorporates a predictive reactive site, and assaying the new molecule as described above.

The following Examples provide an illustration of embodiments of the invention and should not be construed to limit the scope of the invention which is set forth in the appended claims. In the following Examples, all methods described are conventional unless otherwise specified.

EXAMPLE 1

Purification of the TNF-α Converting Enzyme

This Example describes a method for purifying TACE. The TACE was isolated and purified from the membranes of the human monocytic cell line, THP-1, (ATCC no. TIB 202) that had been stimulated to produce TNF-α. THP-1 cells were chosen because they produce more TNF-α than HL-60 cells, a more commonly used human monocytic cell line. Approximately 120 billion cells were stimulated using the procedure previously described by Kronheim et al., *Arch. Biochem. Biophys.* 269:698 (1992), incorporated herein by reference. Two hours after stimulation, the cells were harvested by centrifugation. The harvested cells were washed at least twice with Hanks balanced salt solution, and plasma membranes were isolated according to method number three as described by Maeda et. al., *Biochim. et. Biophys. Acta*, 731:115 (1983), except that dithiothreitol was not used, utilizing 1.25 ml of homogenization buffer per ml of cell pellet. It was determined that the standard procedure of Maeda et al., Id., utilizing dithiothreitol, failed to yield compounds having TACE activity (an assay for TACE activity is described below). Proteins were then solubilized by resuspending the membrane preparation in a solution of 1% octylglucoside, 10 mM Tris-HCl (pH 8), 1 mM MgCl$_2$ and 30 mM NaCl and briefly homogenizing with a Brinkman Homogenizer (twice, five seconds each time). Phospholipids were then extracted by adding four volumes of ice-cold (0° C.) acetone; after a thirty-minute incubation at 4° C., the acetone-extracted material was centrifuged at 1500 rpm for 10 minutes in a H1000B rotor.

Chromatography

The pelleted material was dissolved in 450 ml of Buffer A (Buffer A comprises 10 mM Tris-HCl (pH 7.5) and 1% octylglucoside (weight to volume percent)) and applied to a 120 ml column of DEAE-Sepharose fast-flow (Pharmacia) at 4 ml per minute. The column then was washed with 360 ml of Buffer A at 6 ml per minute, and protein was then eluted with an increasing gradient of NaCl (0–0.3 M) in Buffer A applied at 6 ml per minute over a period of 40 minutes. TACE was eluted with a NaCl concentration of about 50 to about 150 mM.

TACE was originally detected at this point by its ability to cleave recombinant 26 kD TNF-α fused to the "flag" (T. P. Hopp, et al., *Bio Technology*, 6:1204 (1988) sequence of 8 amino acids at the amino-terminus. The gene encoding human TNF-α was spliced to DNA encoding the flag sequence, and this construct was placed in the pPL3 vector (C. Maliszewski et al., *Molec. Immunol.*, 25:429 (1987). The protein was then expressed in a protease-deficient strain of *E. coli* (R. T. Libby et al., *DNA*, 6:221 (1987) which was found necessary to prevent degradation of the precursor by the bacteria. After removal of growth medium, the bacteria were resuspended in 30 mM Tris-HCl (pH 8), 5 mM EDTA, and the suspension was sonicated for about 30 seconds. The material was then centrifuged at 20,000 rpm in an SS34 rotor for 30 minutes, the supernatant fraction was discarded, and the pellet was resuspended with 8 M urea in 10 mM Tris-HCl (pH 8). The material was homogenized with 25 strokes in a dounce homogenizer and then centrifuged at 20,000 rpm in an SS34 rotor for 30 minutes. The supernatant fraction, which contained the precursor TNF-α, was then dialyzed four times against 10 mM Tris-HCl (pH 8).

This material was incubated at 37° C. for at least 4 hours with the TACE eluted from the DEAE-Sepharose, that had been treated with 1 mM N-methoxysuccinyl-Ala-Ala-Val-chloro-methylketone, 10 µg/ml leupeptin, and 1 mg/ml α1-protease inhibitor, all of which are commercially available. The N-terminus of the resulting 17 kD product was found to be that of authentic TNF-α. After the initial identification of TACE in this way, it was found that the enzyme also cleaves an 8-residue peptide representing the segment Leu$^{73}$-Ala$^{74}$-Gln$^{75}$-Ala$^{76}$-↓-Val$^{77}$-Arg$^{78}$-Ser$^{79}$-Ser$^{80}$ (SEQ ID NO:5) of TNF-α Wherein the (↓) illustrates the cleavage site. Based on this observation, a quantitative assay was established: the peptide, at 1 mM, was incubated with the enzyme at 37° C. for a fixed period of time, in the presence of 0.1 mM dichloroisocoumarin, 1 mM methoxysuccinyl-Ala-Ala-Pro-Val-chloromethyl-ketone, 10 µg/ml leupeptin, 10 µM bestatin, and 1 mg/ml α1-protease inhibitor (Sigma), all of which are commercially available. The reaction was then stopped by the addition of acid or a metal chelator. The extent of cleavage of this peptide, reflecting the amount of TACE present, was determined by applying the mixture to a Vydac C18 column and eluting with a gradient of 0 to 30% acetonitrile over a period of 15 minutes.

Material that eluted from the DEAE column with 0.05–0.25 M NaCl had about a 4-fold higher specific activity than the starting material. The eluted material was sonicated and then shaken with wheat germ agglutinin-agarose (Vector Laboratories) for two hours at 4° C. Prior to use, the wheat germ agglutinin-agarose was washed with 5 column volumes of Buffer B (Buffer B comprises 10 mM Tris-HCl (pH 7.5), 0.15 M NaCl, 0.1 mM MnCl$_2$, 0.1 mM CaCl$_2$, 1% octylglucoside and 10% glycerol); 1 ml of this resin was used for every 2 mg of protein in the sample, as determined by the BCA protein assay (Pierce). After two hours, the resin was washed with 7 volumes of Buffer B, and material was then eluted with 5 column volumes of Buffer B plus 0.3 M acetyiglucosam-ine (Sigma), with 30 minute intervals between the application of each column volume.

Eluted fractions contianing TACE activity had about a ten-fold higher specific activity than the starting material. These fractions were concentrated to about 5 ml with Centriprep-30 concentrators (Amicon) and then diluted three-fold with Buffer C (Buffer C comprises 10 mM Tris-HCl (pH 8), 1% octylglucoside and 10% glycerol). The diluted material was sonicated (three 10-second bursts) and then loaded onto a MonoQ HR 5/5 column (Pharmacia) at 0.5 ml per minute. The column was then washed with 10 ml of Buffer C at 0.5 ml per minute, and material was eluted with a 0 to 0.25 M NaCl gradient in Buffer C at 0.5 ml per minute over a period of 30 minutes. TACE activity (detected at this stage and subsequently by incubation with the previously described peptide substrate in the absence of protease inhibitors) eluted with about 0.15M NaCl.

The NaCl concentration in the MonoQ fractions containing activity was reduced by at least ten-fold by diluting the material into Buffer C, and the material was then applied to a column of hydroxyapatite (American International Chemical, ceramic hydroxyapatite HS40) at the rate of 0.5 ml per minute. After washing with three column volumes of Buffer C, protein was eluted with a 0 to 50 mM gradient of sodium phosphate at 1 ml per minute over a period of 30 minutes. TACE eluted with about 15 mM sodium phosphate.

The TACE eluted from the hydroxyapatite column was then concentrated to about 100 µl with Centricon-50 concentrators (Amicon) and applied to a Bio-Rad SEC-400 sizing column (30 cm). Protein was eluted with Buffer C run through the column at 0.5 ml per minute; TACE eluted at about 28 minutes.

The TACE eluted from the sizing column was diluted three-fold into Buffer D (Buffer D comprises 20 mM MES (pH 6), 1% octyglucoside and 10% glycerol) and applied to a 1 ml column of Red 120-agrose (Sigma) at 0.25 ml per minute. After the column was washed with 10 ml Buffer D, protein was eluted with a 0 to 1 M NaCl gradient in Buffer D at 0.25 ml per minute over a period of 60 minutes. TACE eluted with 0.2 to 0.3 M NaCl. Five percent of each eluted fraction was run on a SDS-polyacrylamide gel (10%), and silver staining showed that the predominant protein in the fractions with activity ran approximately midway between the 66 and 97 kD markers (Novex) on the gel, at approximately 80 kD.

Trifluoroacetic acid (TFA) was added to 0.2% (volume-to-volume percentage) to a pool of the fractions containing the approximately 80 kD protein, and the mixture was then pumped onto a 2.1×5 cm C4 column at approximately 100 µl per minute using a Shimadzu LC-10AD. Protein was eluted with a 0 to 100% gradient of acetonitrile in 0.1% TFA at 100 µl per minute over a period of 100 minutes. One minute fractions were collected and 5 to 10% of each fraction was run on a Novex SDS-polyacrylamide gel (10%). Fractions that eluted with about 70% acetonitrile and that contained a protein of approximately 80 kD were pooled and evaporated to dryness.

Generation of peptides and sequencing

This pool of fractions then was dissolved in 200 µl of 50 mM Tris-HCl (pH 8), 1 mM EDTA, and an amount of endo-LYS-C (Promega) equal to about 1/50 of the amount of protein in the sample was added. The material was incubated at 37° C. overnight, and then a fresh aliquot of the same amount of endo-LYS-C was added for an additional 3 hours at 37° C.

The resulting peptides were separated by applying the material to a capillary C18 column at 20 µl per minute and eluting with an ascending gradient of acetonitrile (0.5% per minute) in 0.1% TFA over a period of 200 minutes. Peptides were sequenced with an ABI 476 or an ABI 494 automated sequencer.

EXAMPLE 2

Preparation of Isolated and Purified TACE

This Example describes a method for further purifying the purified TACE as was obtained using the procedures described above. Purified TACE obtained from the THP-1 cells may contain small amounts of human lysosomal 85 kD sialoglycoprotein (*Biochem. Biophys. Res. Commun.* 184: 604–611 (1992) and human lysosomal alpha-mannosidase (*Biochem. Biophys. Res. Comm.* 200:239–245 (1994) that can be removed using standard immunoadsorbant procedures, as described in, for example, Robert K. Scopes, *Protein Purification—Principles and Practice* (Springer-Verlag, 2nd edit.), pp. 167–172. Using the procedures described in this Example 2, isolated and purified TACE can be obtained.

EXAMPLE 3

Cloning of Human TACE

This example describes a procedure for isolating a DNA sequence encoding human TACE. A random primed cDNA library was generated from the commercially available cell line THP-1 (Amersham) using conventional methods. Polymerase chain reaction (PCR) (Mullis and Faloona, *Meth. Enzymol.* 155:335–350, 1987) amplifications were performed using the following primers:

```
Primer (1): 5'-AARTAYGTNATGTAYCC-3'     SEQ ID NO:6

Primer (2): 5'-CCRCARTCRCAYTCYTC-3'     SEQ ID NO:7
```

Primer (1) is based on the first five amino acids of Peptide (2) with the addition of a triplet coding for lysine at the 5' end. Primer (2) is antisense to a conserved amino acid sequence Glu-Glu-Cys-Asp-Cys-Gly (EECDCG) SEQ ID NO:8, which is found in a homologous metalloprotease, bovine reprolysin 1 (GenBank Accession #Z21961).

Single stranded cDNA was amplified using the mixed oligonucleotides described above under standard PCR conditions. The PCR reaction products were fractionated by gel electrophoresis and DNA bands of approximately 180 bp were isolated and subcloned into commercially available pBLUESCRIPT. Sequencing revealed a clone that contained a nucleotide sequence that codes for the amino acids Ile-Ala-Val-Ser-Gly-Asp-His-Glu-Asn-Asn-Lys (SEQ ID NO:9) and a nucleotide sequence that codes for amino acids Glu-Glu-Cys-Asp-Cys-Gly (EECDCG) (SEQ ID NO:8). This clone was termed the "30CD clone." The 30CD clone was sequenced and primers were generated based on this sequence. The primers then were used to detect TACE cDNA in phage library made from human KB cells. This library was screened under conventional conditions using a probe based on the 30CD sequence. Positive hybridizing plaques were isolated and DNA fragments of these clones were sequenced. Sequencing provided a full length cDNA of human TACE which is shown in SEQ ID NO:1. Human TACE was found to be a type I transmembrane protein of 824 amino acids, including a N-terminal 17 amino acid signal peptide. The signal peptide is followed by an extracellular domain of 654 amino acids, a 23 amino acid transmembrane domain and a 130 amino acid cytoplasmic domain. An alternate spliced variant was cloned and sequenced and found to contain the same amino acid sequence as TACE, except that a 50 bp fragment is deleted at the 5' end of the cytoplasmic domain, thus shifting the reading frame to encode a six amino acid cytoplasmic domain. The amino acid sequence of this variant is shown in SEQ ID NO:4, with the cDNA shown in SEQ ID NO:3.

EXAMPLE 4

Preparation of Antibodies Against TACE

This Example describes a method for generating monoclonal antibodies against TACE. Balb/c mice are injected intraperitoneally on two occasions at 3 week intervals with 10 ug of isolated and purified TACE of Example 1 or peptides based on the amino acid sequence of TACE in the presence of RIBI adjuvant (RIBI Corp., Hamilton, Mont.). Mouse sera are then assayed by conventional dot blot technique or antibody capture (ABC) to determine which animal is best to fuse. Three weeks later, mice are given an intravenous boost of 3 ug of human TACE, or TACE peptide, suspended in sterile PBS. Three days later, mice are sacrificed and spleen cells fused with Ag8.653 myeloma cells (ATCC) following established protocols. Briefly, Ag8.653 cells are washed several times in serum-free media and fused to mouse spleen cells at a ratio of three spleen cells to one myeloma cell. The fusing agent is 50% PEG: 10% DMSO (Sigma). Fusion is plated out into twenty 96-well flat bottom plates (Corning) containing HAT supplemented DMEM media and allowed to grow for eight days. Supernatants from resultant hybridomas are collected and added to a 96-well plate for 60 minutes that is first coated with goat anti-mouse Ig. Following washes, $^{125}$I-TACE is added to each well, incubated for 60 minutes at room temperature, and washed four times. Positive wells can be subsequently detected by autoradiography at −70° C. using Kodak X-Omat S film. Positive clones can be grown in bulk culture and supernatants are subsequently purified over a Protein A column (Pharmacia).

What is claimed is:

1. An isolated antibody that binds to a polypeptide comprising an amino acid sequence selected from the group consisting of:

(a) the amino acid sequence of SEQ ID NO:2;

(b) the amino acid sequence of SEQ ID NO:2 from amino acid 215 to amino acid 477;

(c) the amino acid sequence of SEQ ID NO:4;

(d) an amino acid sequence that is at least 90% identical to the amino acid sequence of any of (a)–(c), such that a polypeptide consisting of said amino acid sequence is capable of converting TNF-α from the 26 kD form to the 17 kD form;

(e) a fragment of SEQ ID NO:2 such that a polypeptide with an amino acid sequence consisting of said fragment is capable of converting TNF-α from the 26 kD form to the 17 kD form.

2. The antibody of claim 1 wherein the antibody is a monoclonal antibody.

3. The antibody of claim 1 wherein the antibody is a polyclonal antibody.

4. An isolated polypeptide comprising a Fab fragment of the antibody of claim 1.

5. An isolated polypeptide comprising a F(ab')$_2$ fragment of the antibody of claim 1.

6. The antibody of claim 1 wherein the antibody is a humanized antibody.

7. The antibody of claim 1, wherein the antibody binds to a polypeptide capable of converting TNF-α from the 26 kD form to the 17 kD form, and inhibits said TNF-α converting activity of said polypeptide.

8. A substantially purified antibody that binds to a polypeptide comprising the amino acid sequence of SEQ ID NO:2 from amino acid 215 to amino acid 477.

9. The antibody of claim 8 wherein the antibody is a monoclonal antibody.

10. An isolated polypeptide comprising a Fab fragment of the antibody of claim 8.

11. An isolated polypeptide comprising a F(ab')$_2$ fragment of the antibody of claim 8.

12. The antibody of claim 8 wherein the antibody is a humanized antibody.

13. The antibody of claim 8, wherein the antibody binds to a polypeptide capable of converting TNF-α from the 26 kD form to the 17 kD form, and inhibits said TNF-α converting activity of said polypeptide.

* * * * *